(12) United States Patent
Rabizadeh

(10) Patent No.: US 12,195,808 B2
(45) Date of Patent: Jan. 14, 2025

(54) DYNAMIC CHANGES IN CIRCULATING FREE RNA OF NEURAL TUMORS

(71) Applicant: Nantomics LLC, Culver City, CA (US)

(72) Inventor: Shahrooz Rabizadeh, Agoura Hills, CA (US)

(73) Assignee: NantOmics LLC, Culver City, CA (US)

( * ) Notice: Subject to any disclaimer, the term of this patent is extended or adjusted under 35 U.S.C. 154(b) by 0 days.

(21) Appl. No.: 18/447,117

(22) Filed: Aug. 9, 2023

(65) Prior Publication Data

US 2023/0383366 A1    Nov. 30, 2023

Related U.S. Application Data

(62) Division of application No. 16/639,543, filed as application No. PCT/IB2018/056225 on Aug. 17, 2018, now Pat. No. 11,821,043.

(60) Provisional application No. 62/547,047, filed on Aug. 17, 2017.

(51) Int. Cl.
    *C12Q 1/6886*    (2018.01)

(52) U.S. Cl.
    CPC ..... *C12Q 1/6886* (2013.01); *C12Q 2600/106* (2013.01); *C12Q 2600/112* (2013.01); *C12Q 2600/156* (2013.01); *C12Q 2600/158* (2013.01)

(58) Field of Classification Search
    CPC .................................................. C12Q 1/6886
    See application file for complete search history.

(56) References Cited

FOREIGN PATENT DOCUMENTS

| WO | WO-2016141324 A2 * | 9/2016 | ........... C12Q 1/6886 |
| WO | WO-2017079537 A1 * | 5/2017 | ........... A61K 31/724 |

* cited by examiner

*Primary Examiner* — Kevin E Weddington
(74) *Attorney, Agent, or Firm* — Martin Fessenmaier; Umberg Zipser LLP

(57) ABSTRACT

Circulating free RNA (cfRNA) is used for monitoring status and/or treatment response for neural tumors, and especially glioma, glioblastoma, and neuroblastoma. Particularly preferred cfRNAs include those that encode a marker that is specific to a neural tumor, but also markers that are specific to DNA repair status and/or immune status.

20 Claims, No Drawings

DYNAMIC CHANGES IN CIRCULATING FREE RNA OF NEURAL TUMORS

This application is a divisional application of allowed U.S. application Ser. No. 16/639,543, filed Feb. 14, 2020, which claims priority to our U.S. provisional application having the Ser. No. 62/547,047, filed Aug. 17, 2017, all of which are incorporated in their entirety herein.

FIELD OF THE INVENTION

The field of the invention is methods of monitoring progression, pseudo-progression, and treatment response of neural tumors, especially as it relates to brain tumors such as glioblastoma, glioma and neuroblastoma using circulating free RNA (cfRNA).

BACKGROUND OF THE INVENTION

The background description includes information that may be useful in understanding the present invention. It is not an admission that any of the information provided herein is prior art or relevant to the presently claimed invention, or that any publication specifically or implicitly referenced is prior art.

All publications and patent applications herein are incorporated by reference to the same extent as if each individual publication or patent application were specifically and individually indicated to be incorporated by reference. Where a definition or use of a term in an incorporated reference is inconsistent or contrary to the definition of that term provided herein, the definition of that term provided herein applies and the definition of that term in the reference does not apply.

Neural tumors, especially brain tumors, present a unique challenge to clinicians and researchers as the tumor is often protected within the blood-brain barrier and as such is difficult to reach with pharmaceutical agents. Likewise, monitoring of treatment and tumor progression without direct access to the tumor is typically performed using various imaging methods (e.g., contrast enhanced MM and CT, or magnetic resonance spectroscopy) as most analytes remain behind the blood-brain barrier. Unfortunately, even imaging technologies are at least to some degree dependent on the function of the blood-brain barrier, which is often affected by various drugs. Worse yet, in malignant gliomas, imaging can generally not reliably distinguish treatment-related changes such as radiation necrosis from actual tumor growth. As a result, it is often impossible to make informed decisions on the effect of a specific treatment. Indeed, pseudo-progression is often observed after radiation of high-grade gliomas that can lead a practitioner to premature discontinuation of adjuvant chemotherapy, and even repeat surgery. Conversely, the mirror image of this problem is a pseudo-response that can be seen when edema and blood-brain barrier permeability decrease without an actual reduction in tumor burden.

While it should at least conceptually be difficult for circulating tumor cells to penetrate the blood-brain barrier, indirect evidence suggested that CTCs are indeed present in patients with malignant gliomas. Although metastatic glioblastoma is rarely observed in clinical practice (0.4-0.5% of glioblastoma cases) it can occur, with numerous cases of metastatic glioblastoma reported in the literature. In addition, a number of instances of GBM transmission have been reported in patients who received organ transplants from donors with GBM, and it has been estimated that between 12.5 and 25% of donors with GBM might transmit the tumor (*Neuro Oncol.* 2004; 6:259-263). These cases provide direct evidence that GBM tumor cells were present in donated organs at the time of transplant surgery and the cells must have migrated out of the brain via the bloodstream. Unlike in other solid tumors, however, CTCs have not yet been successfully detected in patients with gliomas.

Circulating proteins have been used as tumor markers in a variety of cancers. Many proteins that are possible biomarkers for glioma were initially identified as markers of traumatic or hypoxic brain injury. A prototype glial-specific marker is glial fibrillary acidic protein (GFAP). Serum levels of GFAP increase after stroke and traumatic brain injury and appear to also be increased in the blood of patients with high-grade gliomas. A study of patients undergoing surgery for suspected glioma, however demonstrated that serum GFAP increases after resection regardless of tumor grade, suggesting that increased serum GFAP is a marker of brain injury and not a specific marker of tumor. Still further protein and nucleic acid markers useful for biopsy materials are described in EP 2260303, US 7754426, and US 2003/0108915.

It is also well known that cancers shed DNA into the bloodstream, and circulating tumor DNA (ctDNA) has been demonstrated in a number of solid tumors, including colorectal cancer and breast cancer. ctDNA can be a highly sensitive and specific biomarker (see e.g., *Nat Med.* 2008; 14:985-990). Several pilot studies have shown that circulating tumor DNA can be detected in the blood of patients with malignant gliomas, and a more recent study showed that mutated IDH-1 DNA can be detected in the plasma of patients with IDH1-positive gliomas, and that there appeared to be a relationship between higher rates of IDH-1 DNA detectability and blood-brain barrier disruption (*Neurology.* 2012; 79:1693-1698). Moreover, one study analyzed methylation of $O^6$-methyl-guanine-DNA methyltransferase (MGMT), p16, DAPK and RASSF1A in serum and tumor of 28 patients with glioblastoma and showed sensitivity and specificity of over 75% for each of these methylated genes using a methylation-specific (MSP) PCR-based assay (*Clin Cancer Res.* 2003; 9:1461-1468). While conceptually promising, analysis of ctDNA remains difficult with respect to at least sensitivity and specificity of such tests.

Further known plasma-based biomarkers include tumor-derived microRNAs (miRNA). In a study of blood from 20 patients with GBM and 20 age-matched controls, 1158 miRNAs were tested. Notably, two miRNAs were found to be significantly altered in GBM patients, miR-128 (upregulated) and miR-342-3p (downregulated) (*J Neurochem.* 2011; 118:449-457). However, direct association of miRNAs with tumor growth and status is often problematic.

Tumor-derived nucleic acids (and other cellular molecules) can also be found in circulating microvesicles that are directly released from glioblastoma cells. Microvesicles can carry specific genetic information from the tumor into the periphery. For example, specific EGFRvIII could be detected in serum microvesicles from 7 out of 25 patients that were collected on the day of surgery (sensitivity 50%, specificity 87%, compared with EGFRvIII in tissue) (*Nat Cell Biol.* 2008; 10:1470-1476). However, the dynamic range using these markers is unclear, and isolation protocols and with that test results vary significantly.

Therefore, even though numerous methods of diagnostic tests for neural/brain tumors are known in the art, all or almost all of them suffer from various disadvantages. Consequently, there remains a need for improved systems and methods to monitor neural/brain tumors, particularly in a non-invasive manner.

SUMMARY OF THE INVENTION

The inventive subject matter is directed to various compositions, systems, and methods of measuring circulating free RNA (cfRNA) to monitor status and/or treatment of neural tumors, and especially measuring cfRNA for cancer markers (e.g., PD-L1) in glioblastoma, glioma, and neuroblastoma. Notably, the inventors discovered that such cfRNA can be used as a diagnostic marker with high sensitivity, specificity, and large dynamic range to ascertain the status and to monitor treatment of a tumor even where the tumor is protected by the blood-brain barrier.

In one aspect of the inventive subject matter, the inventors contemplate a method of monitoring status or treatment of a neural cancer of a patient in which a sample of a bodily fluid of the patient is first obtained. Then, at least one cfRNA is quantified in the bodily fluid of the patient, wherein the cfRNA is specific to at least one of the neural cancer, a DNA repair status, and an immune status. Where desired, the barrier property of the blood-brain barrier in the patient may be modulated (e.g., to increase cfRNA in the circulation).

Most typically, the bodily fluid is whole blood, plasma, or serum, and the neural cancer is a glioma, a glioblastoma, or a neuroblastoma. While not limiting to the inventive subject matter, the cfRNA is from a neural tumor cell and especially contemplated cfRNAs encode at least a portion of MGMT, IDH1, EGFR, p53, PI3K, Rb, RAF, CD133, CD15, A2B5, nestin, ALDH1, ELTD-1, VEGF, PTEN, cytochrome c oxidase, MYCN, CD44, TrkA, LDH, and/or NSE. Of course, it should be noted that suitable cfRNAs include full length versions, splice variants and all known and idiosyncratic mutations thereof.

Additionally, or alternatively, the cfRNA may also be associated with DNA repair (e.g., with base excision repair, mismatch repair, nucleotide excision repair, homologous recombination, and/or non-homologous end-joining), and/or with an immune status of the patient (e.g., cfRNA encodes at least a portion of a PD-L1 gene). Thus, it should be appreciated that contemplated methods may also include a step of measuring at least one additional cfRNA in the bodily fluid of the patient (e.g., housekeeping or reference gene). As appropriate, one or more ratios may be calculated where more than one cfRNA is measured (e.g., PD-L1 to beta actin).

In another aspect of the inventive subject matter, the inventors contemplate a method of determining a prognosis of a neural cancer of a patient from the sample of a bodily fluid of the patient. In this method, a first sample of a bodily fluid of the patient is obtained, and a plurality of changes of one or more cfRNA in the first sample is detected. Most preferably, wherein the bodily fluid is at least one of whole blood, plasma, serum, and cerebrospinal fluid and/or the cfRNA is specific to at least one of the neural cancer, a DNA repair status, and an immune status. Then, the prognosis of the neural cancer can be determined based on at least one of an interrelationship among the plurality of changes and a predetermined threshold of at least one of the plurality of changes. Optionally, the interrelationship among the plurality of changes is measured in a sliding scale. In some embodiments, the method can further include a step of calculating a score for the plurality of changes, and comparing the score with the predetermined threshold.

Most typically, the plurality of changes is selected from a group consisting of a mutation, differential expression of splicing variants, an overexpression, an underexpression, a maturation. In one embodiment, the plurality of changes comprises a mutation in a first cfRNA and an overexpression of a second cfRNA. In such embodiment, the first and second cfRNAs can be derived from two distinct genes. In another embodiment, the plurality of changes comprises expression levels of a first cfRNA and a second cfRNA. In such embodiment, the first and second cfRNAs can be derived from two distinct genes in a same signaling pathway. The first and second cfRNAs are derived from a same type of cell or from different types of cells.

Optionally, the method may also include steps of obtaining a second sample of a bodily fluid of the patient in a different time point than the first sample, detecting a plurality of changes of the one or more cfRNAs in the second sample, and determining the status of an neural cancer by comparing the plurality of changes of the first and second samples. In such embodiment, it is preferred that the plurality of changes of the first and second sample include changes of at least one common cfRNA. Preferably, the different time point can be a post-treatment time point. In such embodiment, the method may further comprise a step of determining an effectiveness of a treatment based on the plurality of changes of the first and second sample.

In some embodiments, the method may further include a step of modulating a barrier property of the blood-brain barrier in the patient. Further, the method may also include a step of predicting a likelihood of success of a treatment regimen based on the prognosis and/or administering a treatment regimen based on the prognosis.

Various objects, features, aspects and advantages of the inventive subject matter will become more apparent from the following detailed description of preferred embodiments.

DETAILED DESCRIPTION

There is an unmet need to evaluate tumor status and treatment response for various brain tumors, and especially glioma, glioblastoma, and neuroblastoma by other means than radiology tests or biopsy from a primary or residual tumor or new metastasis. Advantageously, cfRNA (cell-free RNA that is derived from tumor cells and found as circulating RNA in biological fluids) can be extracted from plasma of cancer patients in less invasive and less complicated manner, and has been emerged as a substitute for a tissue biopsy to obtain information needed for cancer diagnosis. Further, the inventors have now discovered that cfRNA can be used to evaluate tumor status and treatment response for various brain tumors by quantifying numerous marker cfRNAs of brain tumors and their dynamic changes in gene expression.

Thus, in one especially preferred aspect of the inventive subject matter, the inventors contemplate a method of monitoring status or treatment of a neural cancer of a patient using marker cfRNAs obtained from the patient's bodily fluid. Most typically, suitable tissue sources include whole blood, which is preferably provided as plasma or serum. Alternatively, it should be noted that various other bodily fluids are also deemed appropriate so long as cell free nucleic acids, preferably those derived from neural tumors in the central nervous system including neural tumor cells or immune cells in the neural tumor, are present in such fluids. Appropriate fluids include ascites fluid, cerebrospinal fluid, urine, saliva, etc., which may be fresh or preserved/frozen.

Moreover, it is contemplated that where desirable the blood-brain barrier may be modulated with one or more pharmaceutical agents or other treatment modalities (e.g., hyperosmotic agents, focused ultrasound) to increase diffusion or other transport of cfRNA across the blood-brain barrier. Further considerations, suitable cfRNAs, and methods are described in a U.S. provisional patent application having Ser. No. 62/522,615, filed 20 Jun. 2017, to which the international patent application No. PCT/US18/38198 claims priority, a U.S. provisional patent application having Ser. No. 62/513,706, filed 1 Jun. 2017, to which the international patent application No. PCT/US18/31764 claims priority, a U.S. provisional patent application 62/500,497, filed 3 May 2017, to which the international patent application No. PCT/US18/30472 claims priority, and a U.S. provisional patent application 62/522,509, filed 20 Jun. 2017, to which the international patent application No. PCT/US18/22747 claims priority.

Any suitable methods of obtaining cell free nucleic acid including cell free RNA (cfRNA) and/or cell free DNA (cfDNA) from the patient are contemplated. In one especially preferred embodiment, specimens were accepted as 10 ml of whole blood drawn into cell-free RNA BCT® tubes or cell-free DNA BCT® tubes containing RNA or DNA stabilizers, respectively. Advantageously, cfRNA is stable in whole blood in the cell-free RNA BCT tubes for seven days while cfDNA is stable in whole blood in the cell-free DNA BCT Tubes for fourteen days, allowing time for shipping of patient samples from world-wide locations without the degradation of cfRNA or cfDNA. Moreover, it is generally preferred that the cfRNA is isolated using RNA stabilization agents that will not or substantially not (e.g., equal or less than 1%, or equal or less than 0.1%, or equal or less than 0.01%, or equal or less than 0.001%) lyse blood cells. Viewed from a different perspective, the RNA stabilization reagents will not lead to a substantial increase (e.g., increase in total RNA no more than 10%, or no more than 5%, or no more than 2%, or no more than 1%) in RNA quantities in serum or plasma after the reagents are combined with blood. Likewise, these reagents will also preserve physical integrity of the cells in the blood to reduce or even eliminate release of cellular RNA found in blood cell. Such preservation may be in form of collected blood that may or may not have been separated. In less preferred aspects, contemplated reagents will stabilize cfDNA and/or cfRNA in a collected tissue other than blood for at 2 days, more preferably at least 5 days, and most preferably at least 7 days. Of course, it should be recognized that numerous other collection modalities are also deemed appropriate, and that the cfRNA and/or cfDNA can be at least partially purified or adsorbed to a solid phase to so increase stability prior to further processing.

As will be readily appreciated, fractionation of plasma and extraction of cfDNA and cfRNA can be done in numerous manners. In one exemplary preferred aspect, whole blood in 10 mL tubes is centrifuged to fractionate plasma at 1600 rcf for 20 minutes. The so obtained plasma is then separated and centrifuged at 16,000 rcf for 10 minutes to remove cell debris. Of course, various alternative centrifugal protocols are also deemed suitable so long as the centrifugation will not lead to substantial cell lysis (e.g., lysis of no more than 1%, or no more than 0.1%, or no more than 0.01%, or no more than 0.001% of all cells). cfDNA and cfRNA are extracted from 2 mL of plasma using Qiagen reagents. The extraction protocol was designed to remove potential contaminating blood cells, other impurities, and maintain stability of the nucleic acids during the extraction. All nucleic acids were kept in bar-coded matrix storage tubes, with DNA stored at −4° C. and RNA stored at −80° C. or reverse-transcribed to cDNA that is then stored at −4° C. Notably, so isolated cfRNA can be frozen prior to further processing.

Various types of omics data on such obtained patient's cfDNA and/or cfRNA can be generated and changes in the omics data can be determined by comparing the omics data of a healthy individual or the omics data of the patient that is generated at a different time point. As used herein, omics data includes information related to genomics (e.g., DNA sequence information, etc.), and transcriptomics (e.g., RNA sequence information, RNA expression level, splicing variants, etc.). Thus, changes in the omics data may include a change in a DNA or a RNA sequence compared to a healthy individual or the patient's own tissue (e.g., DNA obtained from healthy tissue such as muscle, liver, skin, etc., or cfDNA or cfRNA obtained from different time point), which comprises missense mutation, nonsense mutation, deletion, insertion, duplication, frameshift mutation, repeat expansion, length of poly A tail, etc.). Changes in the omics data may also include a change in expression levels (e.g., upregulation, downregulation, etc.) of RNAs (cellular mRNA or regulatory RNA (e.g., miRNA, etc.)), a change in types or ratios of splicing variants of an mRNA of a gene, or maturation status of the mRNA (e.g., splicing status, length of poly A tail, etc.).

There are numerous methods of genomics and/or transcriptomic analysis known in the art, and all of the known methods are deemed suitable for use herein (e.g., next-generation sequencing (NGS), RNAseq, RNA hybridization arrays, qPCR, etc.). For example, for transcriptomics analysis, preferred materials include mRNA and primary transcripts (hnRNA), and RNA sequence information may be obtained from reverse transcribed polyA$^+$-RNA, which is in turn obtained from a tumor sample and a matched normal (healthy) sample of the same patient. Likewise, it should be noted that while polyA$^+$-RNA is typically preferred as a representation of the transcriptome, other forms of RNA (hn-RNA, non-polyadenylated RNA, siRNA, miRNA, etc.) are also deemed suitable for use herein. Preferred methods include quantitative RNA (hnRNA or mRNA) analysis and/or quantitative proteomics analysis, especially including RNAseq. In other aspects, RNA quantification and sequencing is performed using RNA-seq, qPCR and/or rtPCR based methods, although various alternative methods (e.g., solid phase hybridization-based methods) are also deemed suitable.

Quantification of cfRNA can be performed in numerous manners, however, expression of analytes is preferably measured by quantitative real-time PCR of cf-cDNA using primers specific for each gene. For example, amplification can be performed using an assay in a 10 μL reaction mix containing 2 μL cDNA, primers, and probe. (β-actin can be used as an internal control for the input level of cf-cDNA. A standard curve of samples with known concentrations of each analyte was included in each PCR plate as well as positive and negative controls for each gene. Test samples were identified by scanning the 2D barcode on the matrix tubes containing the nucleic acids. Delta Ct (dCT) was calculated from the Ct value derived from quantitative PCR (qPCR) amplification for each analyte subtracted by the Ct value of actin for each individual patient's blood sample. Relative expression of patient specimens is calculated using a standard curve of delta Cts of serial dilutions of Universal Human Reference RNA set at a gene expression value of 10 (when the delta CTs were plotted against the log concentration of each analyte). Preferably, such measurement of RNA expression level can be normalized with one or more expression level of a housekeeping gene, which is generally known in the art not to be affected or not substantially affected by abnormalities of the central nervous system, including neural tumors. Any suitable housekeeping genes are contemplated, and includes, for example, genes encoding cytoskeletal molecule (e.g., (β-actin, etc.), ubiquitin-related protein (e.g., UBE2D2), a mitochondrial protein (e.g., CYC1, etc.), and/or a ribosomal protein (e.g., RPL13 etc.).

Without wishing to be bound to any specific theory, the inventors contemplate that the development and prognosis of the neural tumor is generally accompanied with one or more changes, preferably at least two changes in cfDNA and/or cfRNA detectable in the bodily fluid of the cancer patient. Preferably, such changes include increase and/or decrease of expression levels of one or more tumor-specific genes, or tumor-specific changes of one or more tumor-related genes. Such finding is particularly unexpected as these tumors are typically insulated from the circulation by the blood-brain barrier that is thought to be a significant obstacle in translocation of molecules the size of cfRNA. Nevertheless, various cfRNA have been detected in patient sera at a relatively large dynamic range with high sensitivity and specificity.

Indeed, there are many suitable cfRNA markers contemplated for monitoring various neural tumors (especially glioma, glioblastoma, and neuroblastoma), and all known RNA sequences and portions thereof that are associated with neural tumors and cancer in general are deemed appropriate cfRNA markers for use herein. Preferably, such cfRNA markers are tumor type specific. For example, suitable markers for glioma include MGMT, 1p/19q, IDH1, EGFR, p53, PI3K, Rb, and RAF, and any known or idiosyncratic mutant form thereof. Likewise, suitable markers glioma stem cells include CD133, Npm1 (nucleiophosmin/B23), CD15, A2B5, nestin, and ALDH1, and any known or idiosyncratic mutant form thereof. Further potential markers as described in *Nature Genetics* 49, 789-794 (2017). Additionally, or alternatively, contemplated glioblastoma markers include ELTD-1, VEGF, PTEN, EGFR, MGMT, IDH1, cytochrome c oxidase, and any known or idiosyncratic mutant form thereof. Additionally, or alternatively, contemplated markers for neuroblastoma include MYCN, CD44, TrkA, LDH, and NSE, and any known or idiosyncratic mutant form thereof.

Further contemplated markers may include those derived from genes related to an immune status of a tumor or a patient, or DNA repair status of the tumor cells. For example, cfRNA molecules with particular relevance to cancer immune therapy, include genes encoding at least a portion of PD-L1, TGF-beta, IL-8, and various other cytokines and chemokines. Therefore, suitable markers also include those that provide information on the immune status (e.g., suppressed, subject to checkpoint inhibition, inflammation, etc.) of a tumor or a patient having the tumor. For example, suitable markers related to immune status may include those associated with checkpoint inhibition, and especially TIM3, LAG3, IDO, TDO, and PD-L1, alone or in any reasonable combination thereof (e.g., PD-L1 with one or more of TIM3, LAG3, IDO, and TDO).

Still further contemplated markers may include those are associated with DNA repair status. Therefore, contemplated cfRNAs include those encoding genes associated with base excision repair (e.g., DNA glycosylase, APE1, XRCC1, PNKP, Tdp1, APTX, DNA polymerase (β, FEN1, DNA polymerase δ or ε, PCNA-RFC, PARP), mismatch repair (e.g., MutSα (MSH2-MSH6), MutSβ (MSH2-MSH3), MutLα (MLH1-PMS2), MutLβ (MLH1-PMS2), MutLγ (MLH1-MLH3), Exo1, PCNA-RFC), nucleotide excision repair (e.g., XPC-Rad23B-CEN2, UV-DDB (DDB1-XPE), CSA, CSB, TFIIH, XPB, XPD, XPA, RPA, XPG, ERCC1-XPF, DNA polymerase δ or ε), homologous recombination (e.g., Mre11-Rad50-Nbs1, CtIP, RPA, Rad51, Rad52, BRCA1, BRCA2, Exo1, BLM-TopIIIα, GEN1-Yen1, Slx1-Slx4, Mus81/Eme1), or non-homologous end-joining (e.g., Ku70-Ku80, DNA-PKc, XRCC4-DNA ligase IV, XLF).

Additional markers may also include various cancer associated markers such as CEA, AFP, and various mutated forms of ras, p53, and/or patient- and tumor-specific mutations that can be identified by comparing omics data for the tumor tissue and corresponding healthy tissue of the same patient. It should be noted that these patient- and tumor-specific mutations may give rise to patient and tumor specific neoepitopes, or may simply be used as patient and tumor specific tracking signals.

In further contemplated aspects, all contemplated cfRNA markers can be associated with or otherwise standardized against a housekeeping or reference gene such as (β-actin cfRNA (e.g., per ml of plasma) that can serve as a proxy measure for total cfRNA in patients. Other suitable exemplary housekeeping genes include HMGB1, beta-2-microglobulin, HSP90AB1, genes encoding tRNA synthetases, genes encoding histones, metabolic genes such as phosphoglycerate kinase, enolase phosphatase, lactate dehydrogenase, etc. Still further housekeeping genes are published elsewhere (e.g., *Trends in Genetics* (2013), Vol. 29, No. 10, pp 569-574). Alternatively, specific ratios of selected markers may be established to monitor treatment with a particular drug (e.g., neoepitope marker versus immune status marker), or to monitor status of the tumor (e.g., glioma specific marker versus apoptosis or necrosis marker). Of course, it should also be noted that the cfRNA marker may be a full-length cfRNA or only a portion thereof.

It is contemplated that the types and numbers of cell free DNA and/or RNA showing changes, and types of changes may vary depending on the type, status (e.g., prognosis, severity, symptoms, etc.) of cancer, and the condition of a patient suffering from the neural cancer (e.g., pre-disposed health conditions, current health conditions, age, sex, geographical area, etc.). Thus, it should be appreciated that one or more desired nucleic acids may be selected for a neural cancer, disease stage of a neural cancer, for monitoring of a specific treatment, for analysis of tumor clonality, presence of a specific mutation, and/or even on the basis of personal mutational profiles or presence of expressed neoepitopes. Alternatively, where discovery or scanning for new mutations or changes in expression of a particular gene is desired, real time quantitative PCR may be replaced by RNAseq to so cover at least part of a patient transcriptome. Moreover, it should be appreciated that contemplated analyses can be performed static, or over a time course with repeated sampling to obtain a dynamic picture without the need for biopsy of the tumor or a metastasis.

For example, a neural tumor can be associated with a mutation in gene A, which results in decrease of RNA expression of gene A. In such case, it is contemplated that the cfRNA obtained from patient's sera may show a mutation (e.g., a point mutation, a deletion, an addition, etc.) and decreased cfRNA quantity compared to a healthy individual with a similar physical conditions (e.g., age, race, ethnicity, health conditions other than cancer, etc.). It is also contemplated that cfDNA obtained from patient's sera may show a mutation (e.g., a point mutation, a deletion, an addition, etc.), yet cfRNA derived from the same gene may not show a mutation if the mutation is located in non-coding area of the gene. In such case, cfRNA may only show decreased cfRNA quantity compared to a healthy individual.

In some embodiments, initiation and development of a neural tumor and/or development of a symptom or neural tumor can be accompanied with a change in sequence (e.g., mutation) and/or an expression level of a cfRNA. In such embodiments, the plurality of changes of the cell free nucleic acid can include at least one nucleic acid sequence changes (e.g., mutation, insertion, deletion, etc.) in a cfDNA or cfRNA, and at least one expression level changes in a cfRNA. It is contemplated that the cfDNA or cfRNA having nucleic acid sequence change(s) may be derived from same gene with the cfRNA showing expression level changes. For example, the patient's blood may include cfDNA that has one missense mutation of gene A, and cfRNA of gene A that shows decreased expression level in the patient's blood. It is contemplated that the cfDNA with a mutation and the cfRNA may be derived from the same portion of the gene A or different portion of the gene A, considering relatively short size of the cell free nucleic acid detected in the blood. In other embodiments, the cfDNA or cfRNA having nucleic acid sequence change(s) may be derived from different gene than the cfRNA showing expression level changes. In such embodiments, it is contemplated that the genes of cfDNA or cfRNA may be functionally related. For example, the patient's blood may include cfDNA that has one missense mutation of gene A, resulting in encoding hypo-phosphorylated protein A, and cfRNA of gene B shows increased expression due to decreased transcriptional inhibition by hypo-phosphorylated protein A. In another example, the patient's blood may include cfDNA that has one missense mutation of gene A, resulting in encoding hypo-phosphorylated protein A, and cfRNA of gene B shows increased expression due to the increased inflammation response by inactive hypo-phosphorylated protein A.

It is also contemplated that the plurality of changes of the cell free nucleic acids can include expression levels of two or more cfRNAs. In some embodiments, the plurality of cfRNAs that has increased or decreased expression levels may be derived from same gene. For example, two cfRNAs are two splicing variants of gene A, and only one cfRNAs may show increased expression level while another cfRNA has static, or even decreased expression level. In other embodiments, the plurality of cfRNAs that has increased or decreased expression levels may be derived from different, distinct genes. In such embodiments, the plurality of cfRNAs that has increased or decreased expression levels may be derived from genes encoding functionally related proteins. For example, two cfRNAs are derived from genes in the same signaling pathway such that one cfRNA is derived from gene A and another cfRNA is derived from gene B, where protein A' encoded by gene A is inhibitory to a signaling pathway that leads to transcription of gene B. For other example, one cfRNA is derived from gene A and another cfRNA is derived from gene B, where protein A' encoded by gene A stabilize the mRNA encoded by gene B.

Alternatively, the plurality of cfRNAs that has increased or decreased expression levels may be derived from genes encoding functionally relevant proteins, yet not necessarily located in the same pathway. For example, one cfRNA is derived from gene C and another cfRNA is derived from gene D, where gene C is involved in the apoptosis pathway and gene D is involved in the inflammatory response pathway. In such example, those two cfRNA expression levels are not inter-regulated directly, yet may concurrently be increased or decreased due to the physiological conditions of the cell.

In addition, the plurality of cfRNAs and/or cfDNAs that show changes can be derived from a same type of cells or different types of cells in the neural tumor. For example, cfRNAs and/or cfDNAs that are changed can be derived from neural tumor cells, immune cells in the neural tumor mass, or any other types of cell that interact or surround the neural tumor cells.

It is contemplated that at least some of such changes can be an indicator of a prognosis of the neural cancer when considered individually and/or collectively. Typically, such changes are quantitatively and/or qualitatively interrelated with each other, while, alone, may not be a decisive factor for determining a prognosis of the neural cancer. As used herein the term "interrelated" or "interrelationship" refers a relation between changes that are shown among patients diagnosed with the neural tumor at a statistically higher chance (e.g., at least 50% of the patients, at least 70% of patients, etc.). Thus, it should be appreciated that the interrelated changes may be causally related (e.g., change A causes change B, etc.) or associated (e.g., change A and change B occurs concurrently without necessarily having a direct or indirect interaction with each other, etc.). For example, a cfRNA derived from a mutated EGFR (e.g., EGFRvIII) gene and a cfRNA derived from a mutated IDH-1 gene can be detected from a patient's blood. A mutation in EGFR may be an indicator of a tumor, but not necessarily of a neural tumor, as EGFR mutations are found in multiple types of tumors (e.g., non-small cell lung cancer, etc.). Similarly, a mutation in IDH-1 may be an indicator of a tumor, but not necessarily of a neural tumor, as IDH-1 mutations are found in multiple types of tumors (e.g., gliomas, glioblastoma, acute myeloid leukemia, thyroid carcinomas, etc.). Yet, the concurrent detection of mutation in EGFR and IDH-1 can be a stronger indicator of neural tumor development.

In another example, from a patient's blood, decreased expression level of cfRNA derived from Adhesion G Protein-Coupled Receptor L4 (ADGRL4) gene and a specific alternatively spliced form of cfRNA derived from Homeobox B3 (HOXB3) can be detected. While decreased transcription of ADGRL4 can be often detected in glioblastoma, it may neither be a decisive factor for glioblastoma development as such change can be observed in different types of tumors. Yet, the concurrent detection of decreased transcription of ADGRL4 and specific alternatively spliced form of HOXB3, collectively, can indicate the recurrent glioblastoma development. In such case, it is contemplated that the prognosis of glioblastoma can be determined based on the magnitude of decreased expression of ADGRL4 (e.g., at least 30%, at least 50%, at least 70%, at least 80% decrease compared to a healthy individual, etc.) and the ratio of the alternatively spliced form of HOXB3 (e.g., at least 30% total HOXB3 mRNA, at least 50% total HOXB3 nRNA, at least 70% total HOXB3 mRNA, etc.), It is also contemplated that a score can be calculated based on the plurality of changes, which can be used to determine prognosis of the neural cancer. In some embodiments, each change of relevant cfDNA and cfRNA may be given a positive or a negative score to add up to generate an overall score of the patient's cell free nucleic acid. For example, where decreased transcription of ADGRL4 and specific alternatively spliced form of HOXB are detected, a cfRNA score for ADGRL4 can be calculated based on the magnitude of the ADGRL4 mRNA expression (e.g., 1 score per 10% decrease, etc.), and cfRNA score for alternatively spliced form of HOXB can be calculated based on the quantity ratio of the alternatively spliced form of HOXB among overall HOXB mRNA (e.g., 1 score per 10% total alternatively spliced form of HOXB among overall HOXB mRNA, etc.). Then, the prognosis of the glioblastoma can be determined (e.g., diagnosed, the progress is confirmed, etc.) when the overall score exceeds a predetermined threshold. In other embodiments, the score can be calculated based on the plurality of changes in a sliding scale. For example, where the prognosis of the glioblastoma can be determined by determining ADGRL4 mRNA expression level and HOXB mRNA alternatively spliced form ratio, the prognosis of the glioblastoma can be determined when the ADGRL4 mRNA expression level is increased over 200%, over 300%, over 400% even if HOXB mRNA alternatively spliced form ratio is less than 20%. Alternatively, the prognosis of the glioblastoma can be determined when the HOXB mRNA alternatively spliced form ratio is more than 70%, more than 80%, more than 90%, even if the ADGRL4 mRNA expression level is increased less than 30%, less than 20%, or less than 10%.

Additionally, the prognosis of a neural tumor can be determined by detecting changes of relevant cfDNA(s) and/or cfRNA(s) over time that reflect relative changes of cfDNA(s) and/or cfRNA(s) in the patient. For example, changes of cfDNA(s) and/or cfRNA(s) can be detected in the first and second samples of the patient, which are obtained at least 1 day, at least 5 days, at least 10 days, at least 30 days, at least 3 months, at least 6 months, at least 1 year apart. The time distance between two samples may vary depending on the type of neural tumors. For example, it is preferred that the time distance is shorter (e.g., 7 days, 2 weeks, 1 month, etc.) for a fast-developing neural tumors (e.g., grade 4 astrocytoma, etc.). For other example, it is preferred that the time distance is relatively longer (e.g., 1 month, 3 months, 6 months, etc.) for a slow-developing neural tumors (e.g., childhood brain tumors, etc.).

While the sets of cell free nucleic acids that may show changes in the first and second sample of the patient may differ depending on the type or prognosis of neural tumors, it is preferred that the sets of cell free nucleic acids may have at least one cell free nucleic acid in common for comparison. For example, the set of cell free nucleic acids in the first sample that show changes may include cfRNAs of gene E and gene F, and the set of cell free nucleic acids in the second sample that show changes may include cfRNAs of gene E and gene G.

The inventors also contemplate that the multiple measurements of the cell free nucleic acids over a period of time can be used to determine the effectiveness or likelihood of successful outcome of the treatment to the neural tumor(s) and/or to provide a recommendation of treatment regimen. For example, changed expression levels of cfRNA derived from gene H and I can be detected before and after a treatment (e.g., a drug treatment, a radiotherapy, a surgery, etc.), or multiple time points before and after the treatment to evaluate the overall trend of changes in the expression levels of cfRNA H and I. The cfRNA H and I's expression levels are both increased during the multiple time points before the treatment. After the treatment, decrease of expression levels of cfRNA derived from gene H could be detected, while the expression level of cfRNA I is relatively static. In such example, a treatment can be considered to be effective to stop or reverse the progress of the neural tumors (as reflected by decrease of cfRNA H). In addition, a treatment regime to affect a pathway involving gene I (e.g., a drug targeting the protein encoded by gene I, a drug targeting the transcription pathway of gene I, a drug targeting a protein upstream or downstream of the protein encoded by gene I, etc.) can be recommended for the next treatment plan or can be administered to the patient to treat the tumor based on the determined prognosis of the tumor with the expression levels of cfRNA H and I or other cell free nucleic acid.

Alternatively and/or additionally, measurement of cfDNA and/or cfRNA can be analyzed in view of one or more a behavioral test data (e.g., motor behavior, sensory perception, etc.), a cognitive test data (e.g., psychometric assessment, etc.), electroencephalography (EEG) data, electromyography (EMG) data, and a MRI and/or CAT scan data. The type and combination of the test data may vary depending on the type of the neural cancer, the suspected location, and/or progress of the neural cancer. For example, for patients suspected to have a neural cancer in a size large enough to be detected as a tumor mass, a CAT scan data and/or a MRI test data may be accompanied or used as supplemental to detection of changes in cfDNA and/or cfRNA. In another example, the functional effect of the neural cancer can be determined by behavioral test data (e.g., neural tumor in cerebellum may be accompanied with the motor behavior disability including loss of balance, etc.) or cognitive test data (e.g., for neural tumors located in the frontal lobe or temporal lobe, etc.).

In some embodiments, the numbers expressing quantities of ingredients, properties such as concentration, reaction conditions, and so forth, used to describe and claim certain embodiments of the invention are to be understood as being modified in some instances by the term "about." Accordingly, in some embodiments, the numerical parameters set forth in the written description and attached claims are approximations that can vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the invention are approximations, the numerical values set forth in the specific examples are reported as precisely as practicable. The numerical values presented in some embodiments of the invention may contain certain errors necessarily resulting from the standard deviation found in their respective testing measurements.

As used herein, the phrase "at least one of A and B" is intended to refer to 'A' and/or 'B', regardless of the nature of 'A' and 'B'. For example, in some embodiments, 'A' may be single distinct species, while in other embodiments 'A' may represent a single species within a genus that is denoted 'A'. Likewise, in some embodiments, 'B' may be single distinct species, while in other embodiments 'B' may represent a single species within a genus that is denoted 'B'.

As used in the description herein and throughout the claims that follow, the meaning of "a," "an," and "the" includes plural reference unless the context clearly dictates otherwise. Also, as used in the description herein, the meaning of "in" includes "in" and "on" unless the context clearly dictates otherwise. Unless the context dictates the contrary, all ranges set forth herein should be interpreted as being inclusive of their endpoints, and open-ended ranges should be interpreted to include commercially practical values. Similarly, all lists of values should be considered as inclusive of intermediate values unless the context indicates the contrary.

It should be apparent to those skilled in the art that many more modifications besides those already described are possible without departing from the inventive concepts herein. The inventive subject matter, therefore, is not to be restricted except in the scope of the appended claims. Moreover, in interpreting both the specification and the claims, all terms should be interpreted in the broadest possible manner consistent with the context. In particular, the terms "comprises" and "comprising" should be interpreted as referring to elements, components, or steps in a non-exclusive manner, indicating that the referenced elements, components, or steps may be present, or utilized, or combined with other elements, components, or steps that are not expressly referenced. Where the specification claims refers to at least one of something selected from the group consisting of A, B, C . . . and N, the text should be interpreted as requiring only one element from the group, not A plus N, or B plus N, etc.

What is claimed is:

1. A method of determining a prognosis of a neural cancer of a patient, comprising:
   obtaining a first sample of a bodily fluid of the patient;
   detecting a plurality of changes of one or more cfRNA in the first sample, wherein the plurality of changes are related to a prognosis of the neural cancer, wherein the cfRNA is specific to at least one of the neural cancer, a DNA repair status, and an immune status, and wherein the neural cancer is a glioma, a glioblastoma, or a neuroblastoma; and
   determining the prognosis of the neural cancer based on an interrelationship among the plurality of changes and/or a predetermined threshold of at least one of the plurality of changes.

2. The method of claim 1, wherein the bodily fluid is at least one of whole blood, plasma, serum, and cerebrospinal fluid.

3. The method of claim 1, wherein the plurality of changes is selected from a group consisting of a mutation, differential expression of splicing variants, an overexpression, an underexpression, a maturation.

4. The method of claim 1, wherein the plurality of changes comprises a mutation in a first cfRNA and an overexpression of a second cfRNA, wherein the first and second cfRNAs are derived from two distinct genes.

5. The method of claim 4, wherein the first and second cfRNAs are derived from two distinct genes.

6. The method of claim 1, wherein the plurality of changes comprises expression levels of a first cfRNA and a second cfRNA.

7. The method of claim 6, wherein the first and second cfRNAs are derived from two distinct genes in a same signaling pathway.

8. The method of claim 6, wherein the first and second cfRNAs are derived from a same type of cell.

9. The method of claim 6, wherein first and second cfRNAs are derived from different types of cells.

10. The method of claim 1, wherein the interrelationship among the plurality of changes is measured in a sliding scale.

11. The method of claim 1, comprising calculating a score for the plurality of changes, and comparing the score with the predetermined threshold.

12. The method of claim 1, further comprising modulating a barrier property of the blood-brain barrier in the patient.

13. The method of claim 1, further comprising:
   obtaining a second sample of a bodily fluid of the patient in a different time point than the first sample, wherein the different time point is a post-treatment time point, and further comprising determining an effectiveness of a treatment based on the plurality of changes of the first and second sample;
   detecting a plurality of changes of the one or more cfRNAs in the second sample, wherein the plurality of changes of the first and second sample include changes of at least one common cfRNA; and
   determining the status of a neural cancer by comparing the plurality of changes of the first and second samples.

14. The method of claim 13, wherein the plurality of changes of the first and second sample include changes of at least one common cfRNA.

15. The method of claim 13, wherein the different time point is a post-treatment time point, and further comprising determining an effectiveness of a treatment based on the plurality of changes of the first and second sample.

16. The method of claim 1, the determining the prognosis of the neural cancer is further based on at least one of a behavioral test data, a cognitive test data, electroencephalography data, and a CAT scan data.

17. The method of claim 1, wherein the cfRNA is a cfRNA from a neural tumor cell and is selected from the group consisting of MGMT, IDH1, EGFR, p53, PI3K, Rb, RAF, CD133, CD15, A2B5, nestin, ALDH1, ELTD-1, VEGF, PTEN, cytochrome c oxidase, MYCN, CD44, TrkA, LDH, NSE, and any mutant form thereof.

18. The method of claim 1, wherein the cfRNA is a cfRNA associated with an immune status.

19. The method of claim 18, wherein the cfRNA encodes at least a portion of a gene encoding at least one of PD-L1, TIM3, LAG3, IDO, and TDO.

20. The method of claim 1, further comprising a step of measuring at least one additional cfRNA in the bodily fluid of the patient, wherein the at least one additional cfRNA encodes beta actin, HMGB1, beta-2-microglobulin, or HSP90AB1.

* * * * *